(12) United States Patent
Wexler

(10) Patent No.: US 11,559,680 B2
(45) Date of Patent: Jan. 24, 2023

(54) ELECTROCHEMICAL REDUCTION OF UNWANTED DEPOSITS

(71) Applicant: OSTEOLYSE, INC., Berkeley, CA (US)

(72) Inventor: Emily Louise Wexler, Berkeley, CA (US)

(73) Assignee: Osteolyse, Inc., Berkeley, CA (US)

( * ) Notice: Subject to any disclaimer, the term of this patent is extended or adjusted under 35 U.S.C. 154(b) by 83 days.

(21) Appl. No.: 16/764,528

(22) PCT Filed: Nov. 16, 2018

(86) PCT No.: PCT/US2018/061652
§ 371 (c)(1),
(2) Date: May 15, 2020

(87) PCT Pub. No.: WO2019/099924
PCT Pub. Date: May 23, 2019

(65) Prior Publication Data
US 2020/0330748 A1    Oct. 22, 2020

Related U.S. Application Data

(60) Provisional application No. 62/588,204, filed on Nov. 17, 2017.

(51) Int. Cl.
*A61N 1/05* (2006.01)
*A61N 1/04* (2006.01)
*A61N 1/20* (2006.01)

(52) U.S. Cl.
CPC ......... *A61N 1/0502* (2013.01); *A61N 1/0496* (2013.01); *A61N 1/20* (2013.01)

(58) Field of Classification Search
None
See application file for complete search history.

(56) References Cited

U.S. PATENT DOCUMENTS

| | | |
|---|---|---|
| 3,842,841 A | 10/1974 | Brighton et al. |
| 2007/0060989 A1 | 3/2007 | Deem et al. |
| 2011/0295100 A1 | 12/2011 | Hegde et al. |
| 2013/0345782 A1 | 12/2013 | Kambouris |
| 2014/0200616 A1* | 7/2014 | Leuthardt ............ A61N 1/0551 606/264 |

(Continued)

FOREIGN PATENT DOCUMENTS

WO    2015/138915 A1    9/2015

OTHER PUBLICATIONS

International Search Report dated Mar. 14, 2019 in related International Application No. PCT/US2018/061652, 1 page.

(Continued)

*Primary Examiner* — Brian T Gedeon
(74) *Attorney, Agent, or Firm* — Kilpatrick Townsend & Stockton LLP

(57) ABSTRACT

This invention relates to devices and methods for the electrochemical removal of unwanted deposits in humans and animals, or for prevention of bone loss following implantation of metal and other surgical materials in the body. A selected voltage is applied using direct current and an electrode to discourage growth or remove deposits, including bone spurs, and may be applied using microneedles in skin contact with a human or animal.

12 Claims, 15 Drawing Sheets

(56) References Cited

U.S. PATENT DOCUMENTS

2016/0375240 A1   12/2016  Yanaki et al.
2017/0028184 A1*  2/2017  Godden ................. A61N 1/327
2017/0231559 A1   8/2017  Cuevas et al.

OTHER PUBLICATIONS

Supplementary European Search Report dated Nov. 25, 2021 in related EP Application No. 18878772.5, 1 page.

* cited by examiner

FIGURE 8
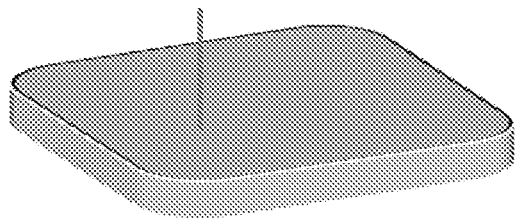
3a. Conductive Medium. hydrogel
1. Cathode
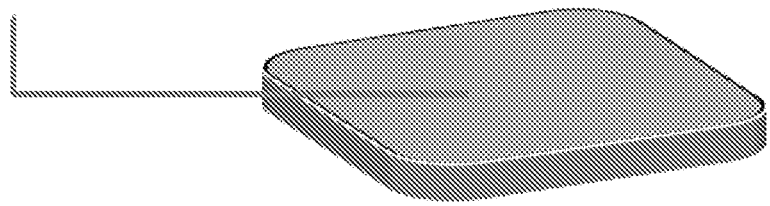
7. Attachment Material
1. Cathode
3. Conductive Medium
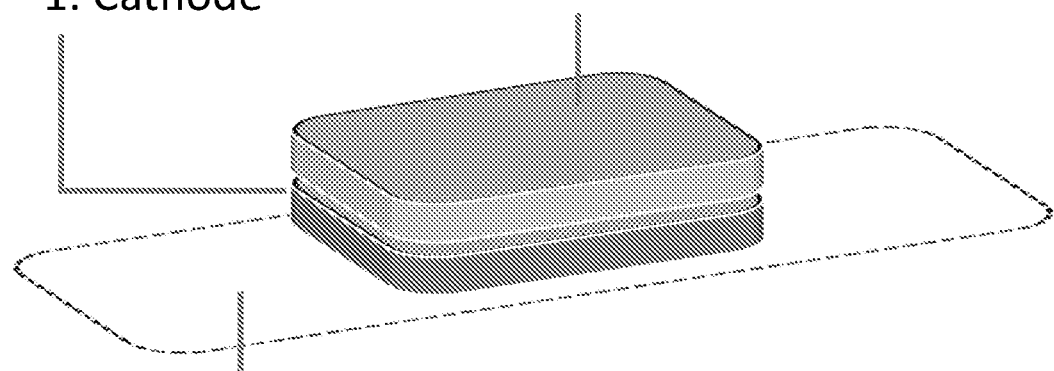
7. Attachment Material

Material Principal applications Metals and alloys

| Material | Principal applications |
|---|---|
| 316L stainless steel, CP-Ti, Ti-Al-V, Ti-Al-Nb, Ti-13Nb-13Zr, Ti-Mo-Zr-Fe | Fracture fixation, stents, surgical instruments Bone and joint replacement, fracture fixation, dental implants, pacemaker encapsulation |
| Co-Cr-Mo, Cr-Ni-Cr-Mo | Bone and joint replacement, dental implants, dental restorations, heart valves |
| Ni-Ti | Bone plates, stents, orthodontic wires |
| Gold alloys | Dental restorations |
| Silver products | Antibacterial agents |
| Platinum and Pt-Ir | Electrodes |
| Hg-Ag-Sn amalgam | Dental restorations |

Ceramics and glasses

| | |
|---|---|
| Alumina | Joint replacement, dental implants |
| Zirconia | Joint replacement |
| Calcium phosphates | Bone repair and augmentation, surface coatings on metals |
| Bioactive glasses | Bone replacement |
| Porcelain | Dental restorations |
| Carbons | Heart valves, percutaneous devices, dental implants |

Polymers

| | |
|---|---|
| Polyethylene | Joint replacement |
| Polypropylene | Sutures |
| PET | Sutures, vascular prosthesis |
| Polyamides | Sutures |
| PTFE | Soft-tissue augmentation, vascular prostheses |
| Polyesters | Vascular prostheses, drug-delivery systems |
| Polyurethanes | Blood-contacting devices |
| PVC | Tubing |
| PMMA | Dental restorations, intraocular lenses, joint replacement (bone cements) |
| Silicones | Soft-tissue replacement, ophthalmology |
| Hydrogels | Ophthalmology, drug-delivery systems |

Composites

| | |
|---|---|
| BIS-GMA-quartz/silica filler | Dental restorations |
| PMMA-glass fillers | Dental restorations (dental cements) |

Abbreviations: CP-Ti, commercially pure titanium; PET, polyethylene tereph-thalates (Dacron, E.I. DuPont de Nemours & Co.); PTFE, polytetra fluoroeth-ylenes (Teflon, E.I. DuPont de Nemours & Co.); PVC, polyvinyl chlorides; PMMA, polymethyl methacrylate; BIS-GMA, bisphenol A-glycidyl.

Materials combinations in total hip replacement (THR) prostheses
 Femoral component Socket component
Co-Cr-Mo
Co-Cr-Mo Alumina/zirconia Alumina
Ti-6Al-4V Surface-coated Ti-6Al-4V
Co-Cr-Mo
UHMWPE UHMWPE Alumina UHMWPE UHMWPE
Widely employed; low wear
Very low wear rate; zirconia more impact resistant
Minimum wear rate (components matched); pain—not in clinical use in the United States
Reports of high UHMWPE wear due to breakdown of titanium surface
Results
Early high loosening rate and limited use; new developments show lowest wear rate (THR only—in clinical use in Europe)
    Enhanced wear resistance to abrasion; only thin treated layer achieved UHMWPE, ultrahigh molecular weight polyethylene. Source: Ref 2

FIGURE 11

Difference of electrochemical potentials between some conductive materials (in mV) in water with 2% salt

| ABSCISSA/ORDINATE | Platinum | Gold/Carbon | Stainless Steel | Titanium | Ag-Hg | Nickel | Copper alloy | Copper | Alu-bronze Brass 30% ZN | Silicon |
|---|---|---|---|---|---|---|---|---|---|---|
| Platinum | 0 | 130 | 250 | 340 | 350 | 430 | 450 | 570 | 600 | 685 |
| Gold/Carbon | 130 | 0 | 110 | 210 | 220 | 300 | 320 | 440 | 470 | 535 |
| Stainless steel | 250 | 110 | 0 | 90 | 100 | 160 | 200 | 320 | 350 | 415 |
| Titanium | 340 | 210 | 90 | 0 | 10 | 90 | 110 | 230 | 260 | 325 |
| Silver-Mercury | 350 | 220 | 100 | 10 | 0 | 80 | 100 | 220 | 250 | 315 |
| Nickel | 430 | 300 | 180 | 90 | 80 | 0 | 20 | 140 | 170 | 235 |
| Copper alloy | 450 | 320 | 200 | 110 | 100 | 20 | 0 | 120 | 150 | 215 |
| Copper | 570 | 440 | 320 | 230 | 220 | 140 | 120 | 0 | 30 | 95 |
| Alu-bronze Brass 30% ZN | 600 | 470 | 350 | 260 | 250 | 170 | 150 | 30 | 0 | 65 |
| Silicon | 665 | 535 | 415 | 325 | 315 | 235 | 215 | 95 | 65 | 0 |
| Brass 50% ZN | 700 | 520 | 520 | 360 | 350 | 270 | 250 | 130 | 100 | 35 |
| Bronze | 770 | 640 | 550 | 430 | 420 | 340 | 320 | 200 | 170 | 105 |
| Tin | 800 | 670 | 590 | 460 | 450 | 370 | 350 | 230 | 200 | 135 |
| Lead | 840 | 710 | 680 | 500 | 490 | 410 | 390 | 270 | 240 | 175 |
| Light alloy NSA 3001 | 940 | 810 | 690 | 600 | 590 | 510 | 490 | 370 | 340 | 275 |
| Steels | 1000 | 870 | 750 | 660 | 650 | 570 | 550 | 430 | 400 | 335 |
| Aluminium A5 | 1090 | 960 | 840 | 750 | 740 | 650 | 640 | 520 | 490 | 425 |
| Cadmium | 1100 | 970 | 850 | 760 | 750 | 670 | 650 | 530 | 500 | 435 |
| Chromium | 1200 | 1070 | 950 | 860 | 850 | 770 | 750 | 630 | 600 | 535 |
| Zinc | 1400 | 1270 | 1150 | 1050 | 1050 | 970 | 950 | 830 | 800 | 735 |
| Manganese | 1470 | 1340 | 1220 | 1150 | 1120 | 1040 | 1020 | 900 | 870 | 805 |
| Magnesium | 1950 | 1620 | 1700 | 1610 | 1600 | 1520 | 1500 | 1380 | 1350 | 1285 |

| |
|---|
| Metal of the abscissa is reduced |
| Very little electrochemistry occurs |
| Metal of the ordinate is reduced |

FIGURE 12

Difference of electrochemical potentials between some conductive materials (in mV) in water with 2% salt

| ABSCISSA ORDINATE | Brass 50% ZN | Bronze | Tin | Lead | Light alloy nSA 3001 | Steels | Aluminium A5 | Cadmium | Chromium | Zinc | Manganese | Magnesium |
|---|---|---|---|---|---|---|---|---|---|---|---|---|
| Platinum | 700 | 770 | 800 | 840 | 940 | 1000 | 1090 | 1100 | 1200 | 1400 | 1470 | 1950 |
| Gold/Carbon | 570 | 640 | 670 | 710 | 810 | 870 | 960 | 970 | 1070 | 1270 | 1340 | 1620 |
| Stainless steel | 450 | 520 | 550 | 590 | 690 | 750 | 840 | 850 | 950 | 1150 | 1220 | 1700 |
| Titanium | 360 | 430 | 460 | 500 | 600 | 680 | 750 | 760 | 860 | 1060 | 1150 | 1610 |
| Silver-Mercury | 350 | 420 | 450 | 490 | 590 | 650 | 740 | 750 | 850 | 1050 | 1120 | 1600 |
| Nickel | 270 | 340 | 370 | 410 | 510 | 570 | 650 | 670 | 770 | 970 | 1040 | 1520 |
| Copper alloy | 250 | 320 | 350 | 390 | 490 | 530 | 640 | 650 | 750 | 950 | 1020 | 1500 |
| Copper | 130 | 200 | 230 | 270 | 370 | 430 | 520 | 530 | 630 | 830 | 900 | 1380 |
| Alu-bronze Brass 30% ZN | 100 | 170 | 200 | 240 | 340 | 400 | 490 | 500 | 600 | 800 | 870 | 1350 |
| Silicon | 35 | 105 | 135 | 175 | 275 | 335 | 425 | 435 | 535 | 735 | 805 | 1285 |
| Brass 50% ZN | 0 | 70 | 100 | 140 | 240 | 300 | 390 | 400 | 500 | 700 | 770 | 1250 |
| Bronze | 70 | 0 | 30 | 70 | 170 | 230 | 320 | 330 | 435 | 630 | 700 | 1180 |
| Tin | 100 | 30 | 0 | 40 | 140 | 200 | 290 | 300 | 400 | 600 | 670 | 1150 |
| Lead | 140 | 70 | 40 | 0 | 100 | 160 | 250 | 260 | 300 | 560 | 630 | 1110 |
| Light alloy NSA 3001 | 240 | 170 | 140 | 100 | 0 | 60 | 150 | 160 | 260 | 460 | 530 | 1010 |
| Steels | 300 | 230 | 200 | 160 | 60 | 0 | 90 | 150 | 200 | 400 | 470 | 950 |
| Aluminium A5 | 390 | 320 | 290 | 250 | 150 | 90 | 0 | 100 | 110 | 310 | 380 | 860 |
| Cadmium | 400 | 330 | 300 | 260 | 160 | 150 | 100 | 0 | 100 | 300 | 370 | 850 |
| Chromium | 500 | 430 | 400 | 360 | 260 | 200 | 110 | 100 | 0 | 200 | 270 | 750 |
| Zinc | 700 | 630 | 600 | 560 | 460 | 400 | 310 | 300 | 200 | 0 | 70 | 550 |
| Manganese | 770 | 700 | 670 | 630 | 530 | 470 | 380 | 370 | 270 | 70 | 0 | 480 |
| Magnesium | 1250 | 1180 | 1150 | 1110 | 1010 | 950 | 860 | 850 | 750 | 550 | 480 | 0 |

| |
|---|
| Metal of the abscissa is reduced |
| Very little electrochemistry occurs |
| Metal of the ordinate is reduced |

ELECTROCHEMICAL REDUCTION OF UNWANTED DEPOSITS

CROSS REFERENCE TO RELATED APPLICATIONS

The present application is a national stage entry under 35 U.S.C. § 371 of International Application No. PCT/US2018/061652, filed on Nov. 16, 2018, which claims the benefit of U.S. Provisional Application Ser. No. 62/588,204, filed on Nov. 17, 2017, which is incorporated by reference herein in its entirety for all purposes.

BACKGROUND OF THE INVENTION

During the lifetime of an animal, development or deposition of solid masses inside the body may occur. Two categories of unwanted deposits include: externally derived deposits and internally derived deposits. Externally derived devices are solids that have been willingly or unwillingly deposited in the body. Some examples of these include medical devices such as stents, braces, splints, screws, pins, and other objects such as shrapnel and bullets. Internally derived deposits are deposits that have formed inside the body as a result of natural processes. Internally derived deposits may interfere with normal daily activities and may cause pain and inflammation in the surrounding tissues. Examples of internally derived deposits include bone spurs, Heberden's and Bouchard's nodules, Calcium Pyrophosphate Crystal Deposition disease (CPPD), Heterotopic Ossification, and many others.

Current treatments for such unwanted deposits include: surgery, drug-based pain management (oral, topical, injection), drug-based inflammation management (oral, topical, injection), manipulation techniques (extracorporeal shockwave therapy [ESWT], high frequency radio waves [HFR], K-laser therapy, physical therapy or physical manipulation). There remains a need for effective treatments for unwanted externally and internally derived deposits.

BRIEF SUMMARY OF THE INVENTION

The present invention provides devices and methods for eliminating or decreasing unwanted deposits in the body of an animal (e.g., a human) and for eliminating or decreasing the loss of bone resulting from medical implants.

According to one embodiment of the invention, a device is provided for eliminating or decreasing unwanted deposits in the body of an animal (e.g., a human). Such unwanted deposits include, but are not limited to, calcium-based deposits and implants. According to one embodiment, such a device comprises: (a) an electrode comprising a material having an electrode potential that is greater than that of the unwanted deposit; and (b) optionally, a power supply that is electrically connected with the electrode, wherein the power supply is configured to provide direct current at a selected voltage; wherein the electrode is configured to contact or to be in electrical connection with the unwanted deposit.

For example, the electrode may be configured to contact the animal's skin. In one such embodiment, the electrode has a surface comprising electrically conductive microneedles configured to penetrate the animal's skin. Such an embodiment may comprise an attachment material for maintaining contact of the electrode with the skin of the animal.

In another such embodiment, the device comprises an electrically conductive layer (e.g., a layer comprising a hydrogel) that has a first surface in contact or in electrical connection with the electrode and a second surface configured to contact the skin of the animal. The second surface of the electrically conductive layer may comprise electrically conductive microneedles configured to penetrate the skin. Such an embodiment may comprise an attachment material for maintaining contact of the electrically conductive layer with the skin of the animal.

In another such embodiment, the electrode of the device is in contact with the unwanted deposit or, alternatively, is connected to the unwanted deposit by an electrically conductive connector, for example, an insulated wire.

According to another embodiment of the invention, methods are provided for eliminating or decreasing unwanted deposits.

According to one such embodiment, a method is provided for eliminating or decreasing the mass of a unwanted deposit in the body of an animal, the method comprising: placing an electrode in electrical connection with the unwanted deposit, wherein the electrode comprises a material having an electrode potential that is greater than that of the unwanted deposit, wherein the electrode is optionally electrically connected with a source of direct current at a selected voltage.

Such a method may comprise contacting the electrode with the animal's skin. Alternatively, the electrode may be in contact with an electrically conductive layer that has a surface in contact with the animal's skin. In yet other alternative embodiments, the electrode is contacted with the unwanted deposit or connected to the unwanted deposit with an electrically conductive connector.

According to another embodiment, impressed current devices and related methods are provided for reducing bone loss caused by an implant.

In one such embodiment, a device is provided for eliminating or decreasing bone loss resulting from an implant in an animal's body comprising a power supply that is electrically connected by an electrically conductive connector with (i) the implant, (ii) an electrode, and/or (iii) a bone of the animal, wherein the power supply is configured to supply direct current at a voltage selected to reduce or eliminate bone loss resulting from the implant.

In another such embodiment, a method is provided for eliminating or decreasing bone loss resulting from an implant in an animal's body, the method comprising: providing a power supply; and electrically connecting the power supply to (i) the implant, (ii) an electrode, and/or (iii) a bone of the animal; wherein the power supply is configured to provide direct current at a voltage selected to decrease or eliminate bone loss resulting from the implant.

According to another embodiment, implants with a sacrificial electrode are provided for reducing bone loss caused by an implant.

In one such embodiment, a medical implant is provided that comprises a sacrificial electrode having an electrical connection with the implant, wherein the sacrificial electrode comprises a material that has an electrode potential that is less than that of bone, and wherein the sacrificial electrode is configured to reduce or eliminate bone loss as compared with a medical implant lacking the sacrificial electrode. As one example, the sacrificial electrode may be configured as a coating on all or a portion of the surface of the implant.

In a related embodiment, methods are provided for making a medical implant with a sacrificial electrode.

In one such embodiment, methods are provided for making a medical implant comprising: (a) providing the implant; and (b) forming an electrical connection between the implant and a sacrificial electrode comprising a material that has an electrode potential that is less than that of bone, wherein the sacrificial electrode is configured to reduce or eliminate bone loss as compared with a medical implant lacking the sacrificial electrode. For example, such a method may comprise attaching to or coating all or part of a surface of the implant with the sacrificial electrode.

In another embodiment, a medical implant is provided that has a surface comprising an electrically non-conductive coating, wherein the coating is configured to prevent an electrical connection between the implant and bone of an animal into which the implant is introduced and thereby reduce or eliminate bone loss as compared with a similar medical implant lacking the coating.

In another embodiment, a method of making a medical implant is provided that comprises (a) providing the implant; and (b) coating the implant with a coating comprising an electrically non-conductive material that is configured to reduce or eliminate bone loss as compared with a similar medical implant lacking the coating.

BRIEF DESCRIPTION OF THE DRAWINGS

FIG. 8 is a schematic drawing showing a device for Heberden's node reduction.

FIG. 10 is a table of materials commonly used in medical applications such as implants.

FIG. 10A is a table of materials commonly used in hip replacement prostheses.

FIG. 11 is a table showing the difference in electrochemical potentials between some conductive materials (in mV) in water with 2% salt.

FIG. 12 is a table showing the difference in electrochemical potentials between some conductive materials (in mV) in water with 2% salt.

DETAILED DESCRIPTION OF THE INVENTION

Figure 1:
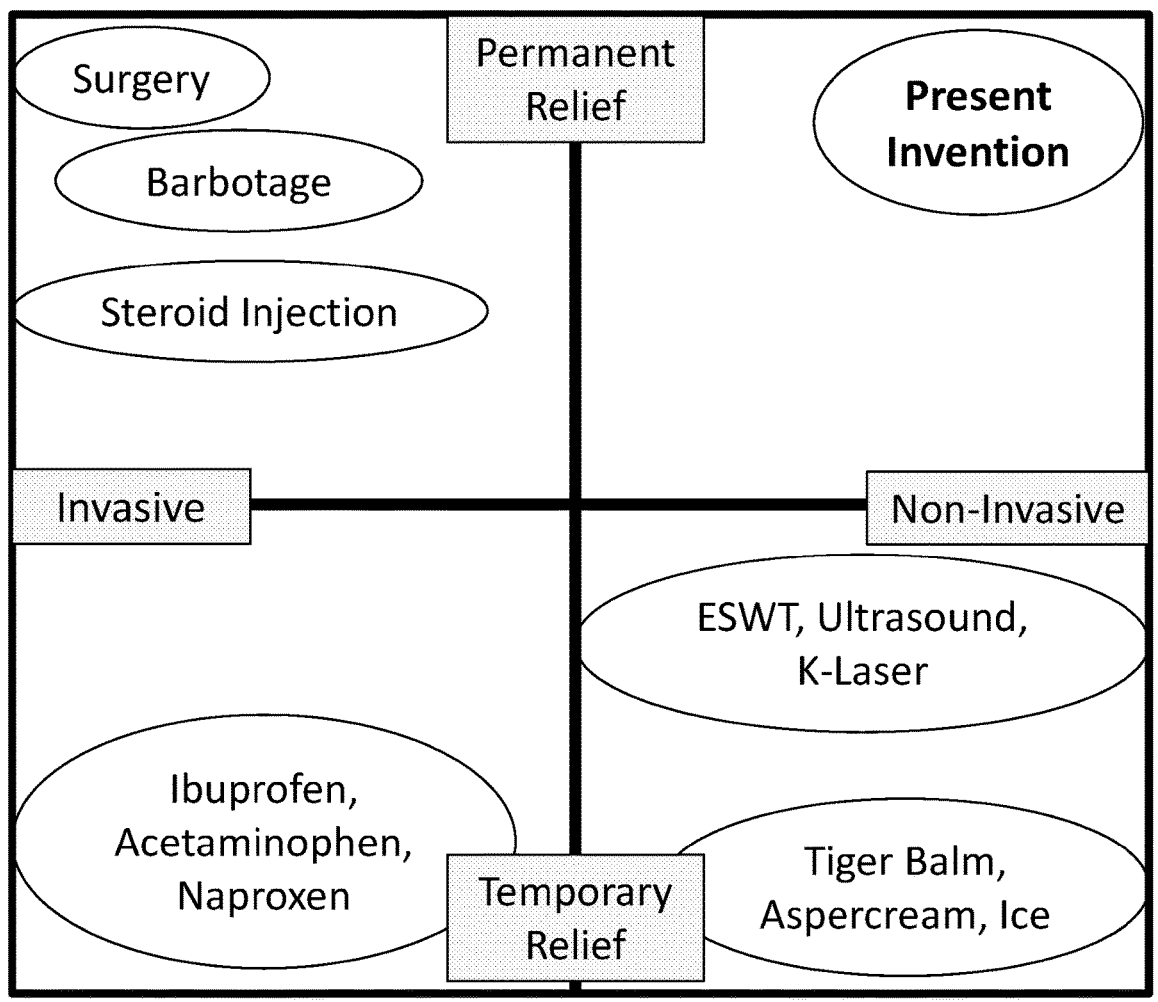
FIG. 1 shows a treatment map for calcification diseases.

For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described. All references cited herein are incorporated by reference into this application in their entirety.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

The term "unwanted deposit" as used herein means (i) a calcium deposit, (ii) another dermal or sub-dermal growth or deposit that is not necessary for normal functioning of the body, such as deposits of hydroxyapatite, calcium oxalate, calcium phosphate, uric acid, magnesium ammonium phosphate (struvite), cysteine, or other materials; (iii) malformed bone unions; (iv) an object that is externally derived and therefore extrinsic to the animal body such as a medical implant, shrapnel, etc. Calcium and other deposits in the body may include other materials, e.g., collagen.

The terms "in electrical connection" or "electrically connected" as used herein means that, in a galvanic cell, two electrodes (an anode and a cathode) are in an electrically conductive medium (e.g., a body fluid, salt water, or other medium) such that an electrical current can pass between the electrodes through the medium. In an electrochemical cell, there is a physical connection between the anode and cathode: they are either in contact with each other or there is an electrical conductor, e.g., a wire that connects them. However, in concrete and other media it has been determined that the physical connection between the anode and cathode are not required for reduction of the anode: the natural potential difference between the anode and cathode when placed in a conductive medium is enough to drive the reduction of the mass of the anode despite their physical separation (see, e.g., Medeiros et al., "Corrosion potential: influence of moisture, water-cement ratio, chloride content and concrete cover," Revista IBRACON de Estruturas e Materiais, 10:864-885, 2017. https://dx.doi.org/10.1590/51983-41952017000400005).

The term "electrically conductive medium" as used herein includes but is not limited to metals, conductive liquids (water, salt water, sea water, saline solution, lactated ringers solution, etc.), gel, hydrogel, lotion, ointment, foam, emulsion, solution, adhesive, cement, conductive microspheres, conductive particulate, conductive fabric or textile, bodily fluids including surface skin moisture, synovial fluid, blood, urine, plasma, or a combination thereof.

The term "hydrogel" is used herein to mean a hydrophilic, three-dimension network used in biomedical practice that is able to imbibe large amounts of water or biological fluids, and thus resembles, biological tissue. Hydrogels are insoluble due to the crosslinking of polymer chains (Ahmed, J. Advanced Research 6:105-121; Chai et al., Gels 3:6, 2017). Any biocompatible hydrogel known in the art may be used in the practice of the invention.

The term "electrode" includes "anodes" and "cathodes." A "cathode" as used herein refers to any material that has a standard electrode potential that is greater than that of the anode in the electrochemical cell completed by the present invention. An electrode may contain a single metal, multiple metals, an alloy of metals, metal oxides, salts, graphite, graphene, a composite material that is electrically conductive as in electroceramics, doped semiconductors or polymers, and others.

The term "electrical contact" is used herein with reference to the materials ability to allow the flow of electrons.

The term "reducing the mass" with regard an unwanted deposit as used herein means the mass of the UD is electrochemically reduced allowing for the dissolution of the UD into the surrounding bodily tissue and fluids, resulting in a net loss of mass of the unwanted deposit.

The term "new bone" as used herein means bone growth that is not part of the normal skeletal structure.

The term "old bone" or "bone" as used herein means bone that is part of the normal skeletal structure.

The terms "standard electrode potential" or "electrode potential" as used herein is a measure of the tendency of a chemical species to acquire electrons and thereby be reduced. Electrode potential is measured in volts (V) or millivolts (mV). Each chemical species has its own intrinsic reduction potential; the more positive the potential, the greater the species' affinity for electrons and tendency to be reduced. The term, "standard electrode potential", as used herein is between −4.101 and +3.27 volts relative to a standard hydrogen electrode under the following conditions (referred to herein as "standard conditions"): a temperature of 298.15 K (25° C.); an effective concentration of 1 mol/L for each aqueous species or a species in a mercury amalgam; and a partial pressure of 101.325 kPa (absolute) (1 atm, 1.01325 bar) for each gaseous reagent. This pressure is used because most literature data are still given for this value rather than for the current standard of 100 kPa. Alternative terminology includes the terms "reduction potential," "redox potential," and "oxidation/reduction potential."

The term "galvanic cell" or "voltaic cell" (or simply "cell") is an electrochemical cell that derives electrical energy from spontaneous redox reactions taking place within the cell. It generally consists of two different metals immersed in an electrolyte, or of individual half-cells with different metals and their ions in solution connected by a salt bridge or separated by a porous membrane.

An activity of unity for each pure solid, pure liquid, or for water (solvent).

A table of standard electrode potentials may be found in CRC Handbook of Chemistry and Physics. 81st Edition Edited by David R. Lida (National Institute of Standards and Technology) CRC Press: Boca Raton, Fl, 2000. ISBN 0-8493-0481-4, Journal of the American Chemical Society p. 8-21 to 8.31.

Overview

"Cathodic protection" (CP) is used for control of the corrosion of metal surfaces by making the metal surface to be protected the cathode of an electrochemical cell. The metal to be protected is electrically connected to or placed in contact with a more easily corroded "sacrificial metal" to act as the anode. The sacrificial metal then corrodes instead of the protected metal.

In cathodic protection, an anode, a piece of a more electrochemically "active" metal, is attached to the vulnerable metal surface where it is exposed to an electrolyte. Galvanic anodes are selected because they have a greater electrode potential than the metal of the target structure. The anode continues to corrode, consuming the anode material until eventually it must be replaced. The driving force for the cathodic protection current is the difference in electrode potential between the anode and the cathode. In order for galvanic cathodic protection to work, the anode must possess a lesser electrode potential than that of the cathode (the target structure to be protected).

For structures such as long pipelines, where passive galvanic cathodic protection is not adequate, an impressed current cathodic protection (ICCP) system may be used. Such a system includes a DC power source (or a transformer-rectifier connected to an AC power source) to provide sufficient current, allowing the rate that the oxidation and reduction reactions occur to be controlled or modulated (increased or decreased).

It is not commonly appreciated that the bone of an animal (e.g., a human) has an electrochemical potential, which can be measured in an electrochemical cell, as is shown in Example 2, in which a bone electrode (anode) is paired with a platinum electrode (cathode). This fact can be exploited to reduce or eliminate the mass of unwanted deposits in the body that have a different standard electrode potential than bone. Conversely, it is possible to reduce or eliminate bone loss resulting from the presence of a medical implant. The present invention provides devices and methods for: (1) eliminating or reducing the size or mass of unwanted externally- or internally-derived deposits (collectively, unwanted deposits or UD) in the body of an animal, e.g., a human; or (2) preventing or reducing the loss of bone in contact with or otherwise affected by an implanted material (e.g., a bone screw or plate, dental implant, hip implant, etc.).

Eliminating or Reducing the Size of Unwanted Deposits

In one embodiment, the present invention provides devices and methods for the electrochemical reduction of unwanted deposits in animals, including humans and non-human animals such as dogs, cats, horses, bovines, pigs, avians, etc. The present invention creates an electrochemical cell where a UD is reduced in vivo. The completed cell will include a cathode, a conductive medium and an anode. Like seawater, animal bodies are electrically conductive. The cathode will be connected electrically to the anode (the UD), thus locally upsetting the natural electrochemical balance.

Electrical potentials of UDs are different from those of healthy bone. Differences in electrical potential are observed in living bone during growth: areas of active growth, repair, or bone apposition during remodeling are electronegative with respect to less active areas. In addition to differing electrical properties, old bone is more highly crystallized than new bone, which may reduce its solubility. Therefore, due to the difference in electrical and physical properties differentiating UDs from healthy bone, we are able to target the UD for selective corrosion.

A treatment map showing the selection of currently available treatments for diseases caused by calcification or mineral deposits is included in FIG. 1. Currently the only permanent treatment for unwanted deposits of this type is surgery. Barbotage, for example, is a minor surgical treatment whereby a needle is partially inserted through the skin and used to physically break apart the calcium deposits on tendons. The treatment map of FIG. 1 places the currently available treatments on a scale of permanence of treatment versus invasiveness of the treatment, it is apparent that there are no available treatments that are both permanent and non-invasive. The apparatus and methods of the present invention meet the need for permanent treatments that can be non-invasive.

Normal Bone Deposition

The skeleton, in addition to providing support for the body, serves as a large store of calcium and phosphate in the form of hydroxyapatite crystals. The calcium phosphate in hydroxyapatite crystals is derived from the blood by the action of bone-forming cells, or osteoblasts. In bone deposition, osteoblasts secrete an organic matrix composed largely of collagen protein, which becomes hardened by deposits of hydroxyapatite. Bone resorption (dissolution of hydroxyapatite) results in the return of bone calcium and phosphate to the blood.

Since the bone matrix contains both an inorganic component (calcium phosphate crystals) and an organic component (collagen and other proteins), the osteoclast must secrete products that both dissolve calcium phosphate and digest the proteins of the bone matrix. The dissolution of calcium phosphate is accomplished by transport of $H^+$ by a $H^+$-ATPase pump in the ruffled membrane, thereby acidifying the bone matrix (to a pH of about 4.5) immediately adjacent to the osteoclast. A channel for $Cl^-$ allows $Cl^-$ to follow the H+, preserving electrical neutrality. Despite the extrusion of $H^+$ from the osteoclast, the cytoplasm is prevented from becoming too basic by the action of an active transport $Cl^-/HCO_3^-$-pump on the opposite surface of the osteoclast.

The protein component of the bone matrix is digested by enzymes, primarily cathepsin K, that are released by osteoclasts. The osteoclast can then move to another site and begin the resorption process again, or be eliminated.

The formation and resorption of bone occur constantly at rates determined by the relative activity of osteoblasts and osteoclasts. Body growth during the first two decades of life occurs because bone formation proceeds at a faster rate than bone resorption. By age 50 or 60, the rate of bone resorption often exceeds the rate of bone deposition. The constant activity of osteoblasts and osteoclasts allows bone to be remodeled throughout life. The position of the teeth, for example, can be changed by orthodontic appliances (braces), which cause bone resorption on the pressure-bearing side and bone formation on the opposite side of the alveolar sockets.

Despite the changing rates of bone formation and resorption, the plasma concentrations of calcium and phosphate are maintained by hormonal control of the intestinal absorption and urinary excretion of these ions. These hormonal control mechanisms are very effective in maintaining the plasma calcium and phosphate concentrations within narrow limits. The maintenance of normal plasma calcium concentrations is important because of the wide variety of effects that calcium has in the body.

Bone Spurs and Calcium-Based Deposits

Bone spurs (osteophytes) are bony projections that develop along bone edges or ends. Bone spurs often form where bones meet each other, i.e., in joints or where tendons or ligaments attach. Bone spur formation has been related to any sequential and consequential changes in bone formation that is due to aging, degeneration, mechanical instability, and disease (such as diffuse idiopathic skeletal hyperostosis). Often osteophytes form in osteoarthritic joints as a result of damage and wear from inflammation. Calcification and new bone formation can also occur in response to mechanical damage in joints. Common locations for bone spurs include the heels, knees, fingers, elbows, hips, shoulders, neck and spine. Osteophytes on the fingers or toes are known as Heberden's nodes (if on the distal interphalangeal joint) or Bouchard's nodes (if on the proximal interphalangeal joints). Bone spurs are commonly associated with conditions such as osteoarthritis, spinal stenosis, spondylosis or plantar fasciitis.

Calcium-based deposits are small, dense areas of calcium that can form after a bone or tissue is stressed or damaged. When an injury or stress occurs, calcium travels through the bloodstream to the injured area to help repair damage. In some cases, the damaged area receives more calcium than is needed. In other cases the microcirculation of the tissue is congested due to the injury: calcium gets into the tissue, but the exiting circulation is restricted and therefore the excess calcium cannot get out, which leads to the deposit. In addition, a tendon may experience chronic tears over a period of time, and the body will deposit calcium to fill the tear. Calcium deposits usually start as a thick paste that eventually hardens if untreated.

Electrochemistry and Dissolution of Unwanted Deposits of Calcium

Body fluids are a conductive medium. Consider an electrochemical cell with a copper (Cu) cathode and a calcium (Ca) anode. The following calculation predicts the spontaneous electrochemical reduction of calcium in solid phase (s) in the presence of solid (s) copper in an aqueous (aq) saltwater solution. Placing a cathode in an electrically conductive medium that contains an unwanted deposit (anode) will reduce the UD.

$$E_{Ca \to Ca+2} + E_{Cu \to Cu2+} = E_{cell}$$

TABLE 1

| Standard Reaction Potentials in Electron Volts (eV) | |
| --- | --- |
| Half Reactions | eV |
| $Ca^{2+}_{(aq)} + 2\ e- \to Ca_{(s)}$ | −2.76 |
| $Ca_{(s)} \to Ca^{2+}_{(aq)} + 2\ e-$ | 2.76 |
| $Cu_{(s)} \to Cu^{2+}_{(aq)} + 2\ e-$ | −0.34 |

Table 1 predicts the spontaneous electrochemical reduction of calcium in solid phase (s) in the presence of solid (s) copper in an aqueous (aq) saltwater solution.

Figure 2:
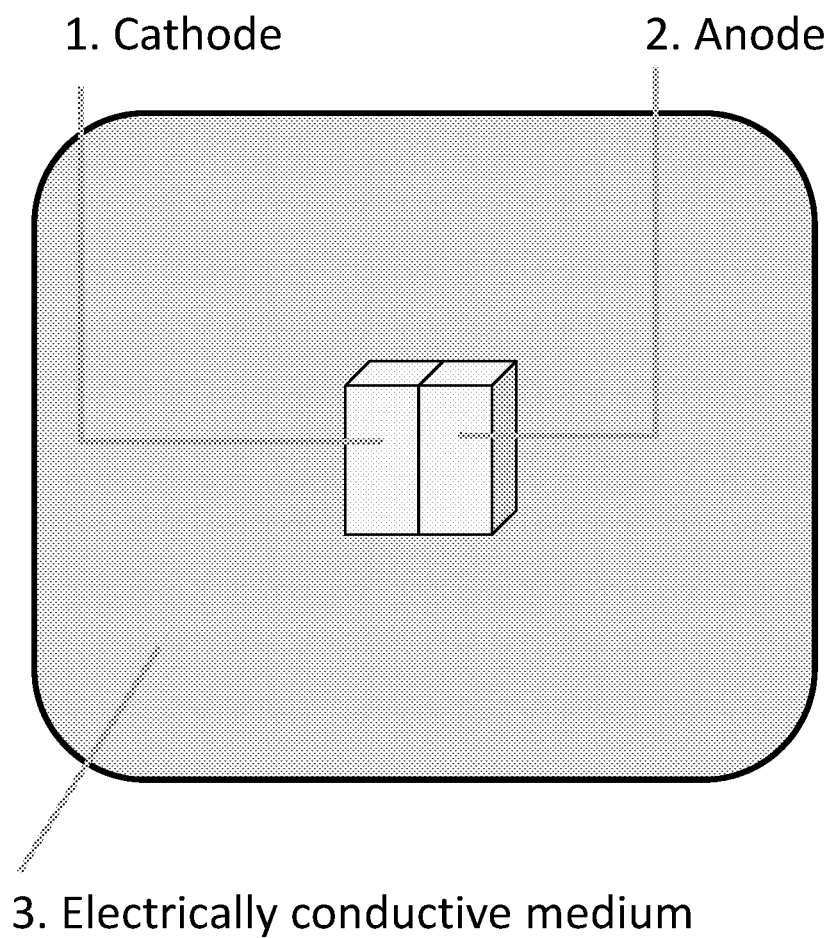
FIG. 2 is a schematic drawing of an electrochemical cell in which the cathode is in direct physical contact with the anode.

Similar principles may be used to remove unwanted deposits in the animal body. One embodiment of the invention is shown in FIG. 2. A cathode is placed (e.g., surgically)

in direct contact with the anode (the unwanted deposit). In the electrically conductive medium of the animal body (including without limitation the skin, body fluids such as synovial fluid, blood, urine, lymphatic fluid, saliva, etc.), the unwanted deposit will be reduced.

Figure 3:
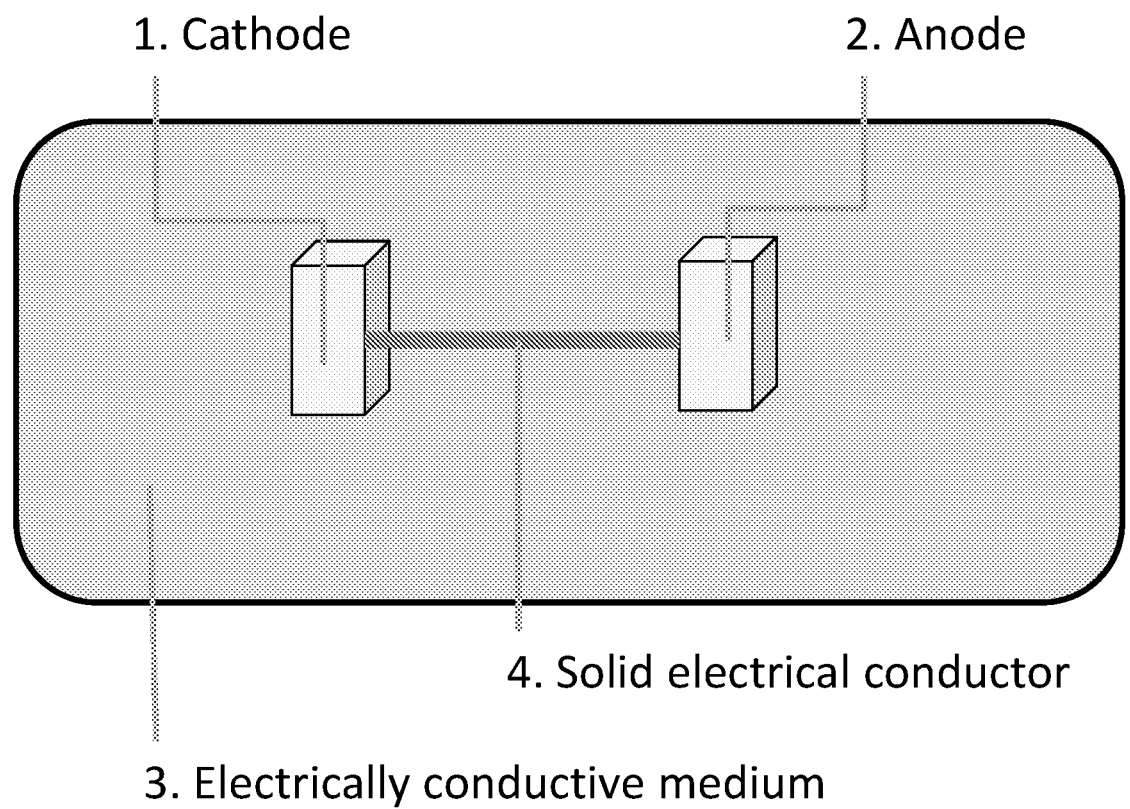
FIG. 3 is a schematic drawing of an electrochemical cell in which the anode and cathode are spaced apart and connected by an electrically conductive connector (e.g., metal wire).

In FIG. 3 an implanted cathode and anode (unwanted deposit) are connected via a solid electrical conductor (e.g., a biocompatible insulated wire) while both are present inside the body.

Figure 4:
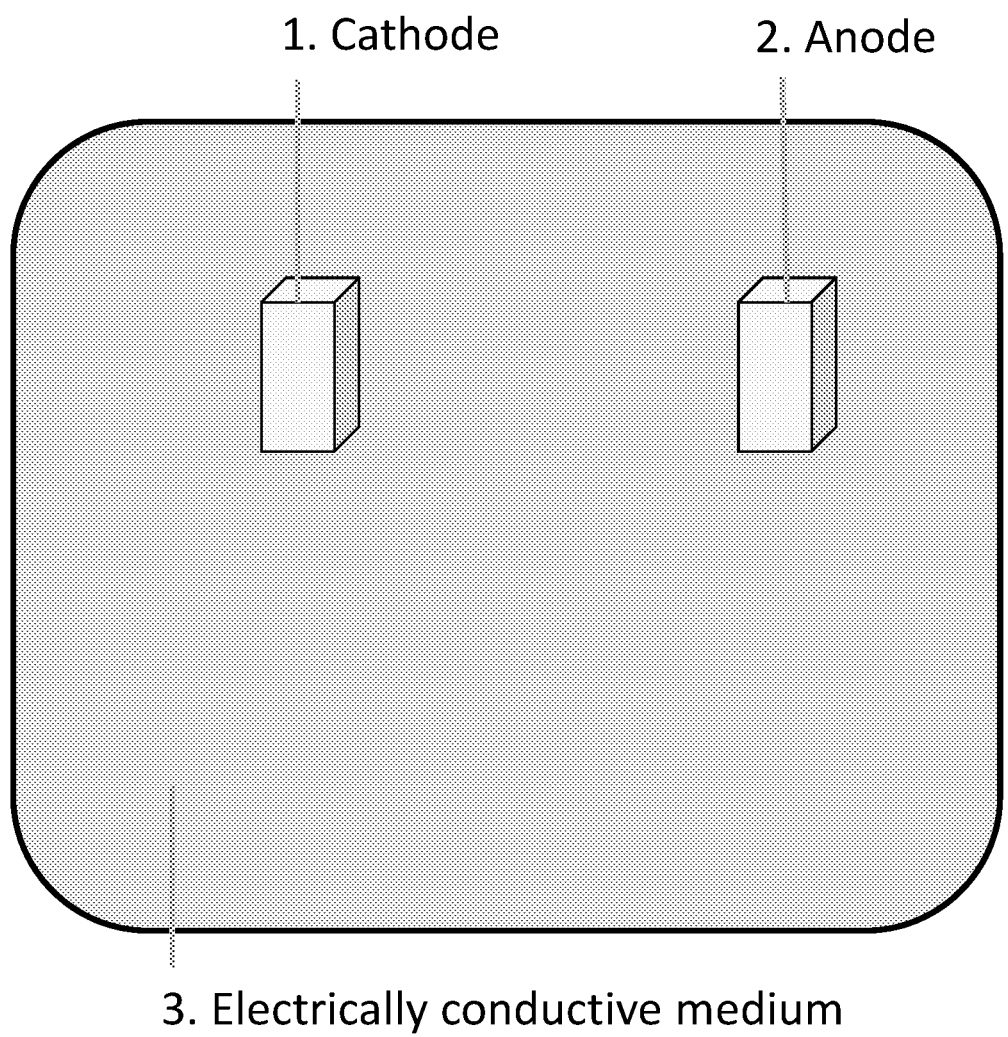
FIG. 4 is a schematic drawing of an electrochemical cell in which the cathode and anode are spaced apart in an electrically conductive medium.

In FIG. 4 the cathode and anode (the unwanted deposit) are both surrounded by the electrically conductive medium (the animal body). Surgical deposition of the cathode in the vicinity of, but not necessarily in direct contact with, the unwanted deposit (anode) will cause reduction of the unwanted deposit.

Figure 5:
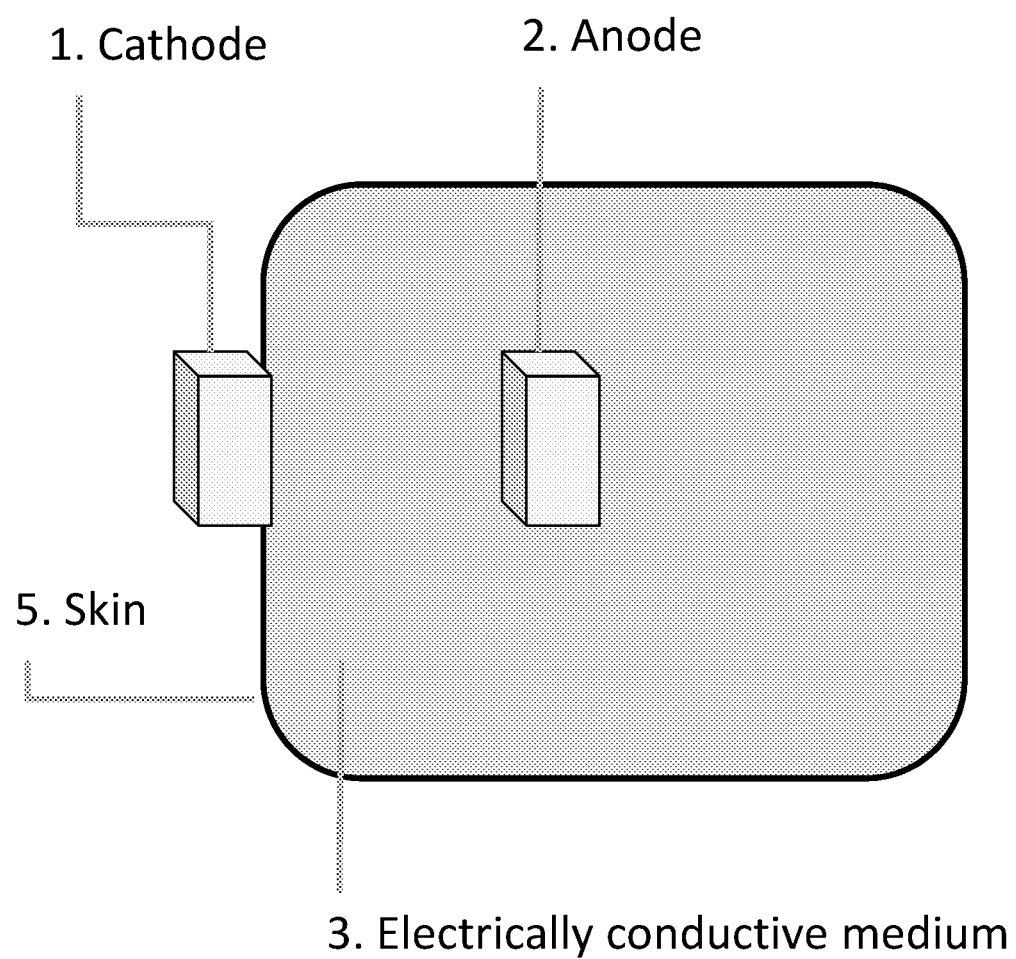
FIG. 5 is a schematic drawing of an electrochemical cell in which the cathode is external to but in contact with the skin and the anode is internal to the animal and surrounded by an electrically conductive medium.

In FIG. 5 the cathode is external to but in contact with the skin, which itself is electrically conductive. The electrical connection is thus from the cathode through the skin and the electrically conductive medium (i.e., the animal body) to the anode (unwanted deposit), thus causing reduction of the anode.

Figure 6:
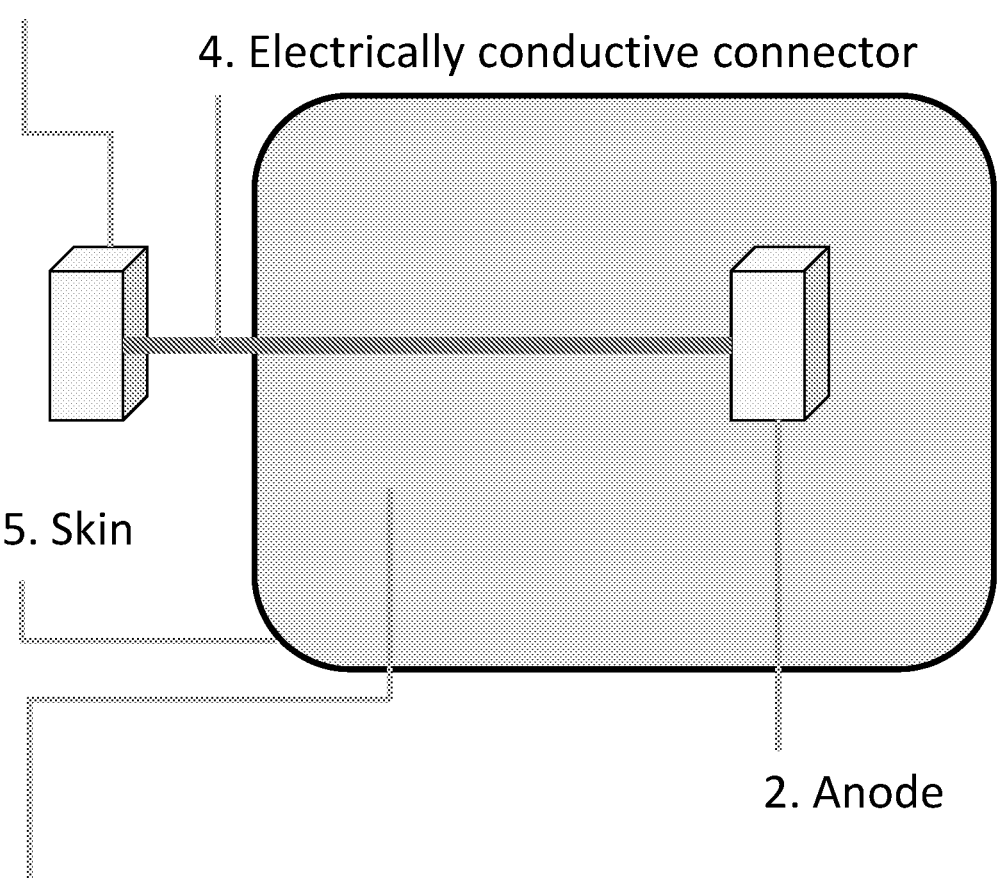
FIG. 6 is a schematic drawing of an electrochemical cell in which the cathode is external to the skin (either spaced apart from or in contact with the skin) and the anode is internal to the animal and surrounded by an electrically conductive medium, and the anode and cathode are connected via an electrically conductive connector.

The configuration shown in FIG. 6 is similar to that shown in FIG. 4 in that the cathode is external to the skin but is directly connected to the anode (unwanted deposit) by a solid electrical conductor (e.g., wire).

Figure 7:
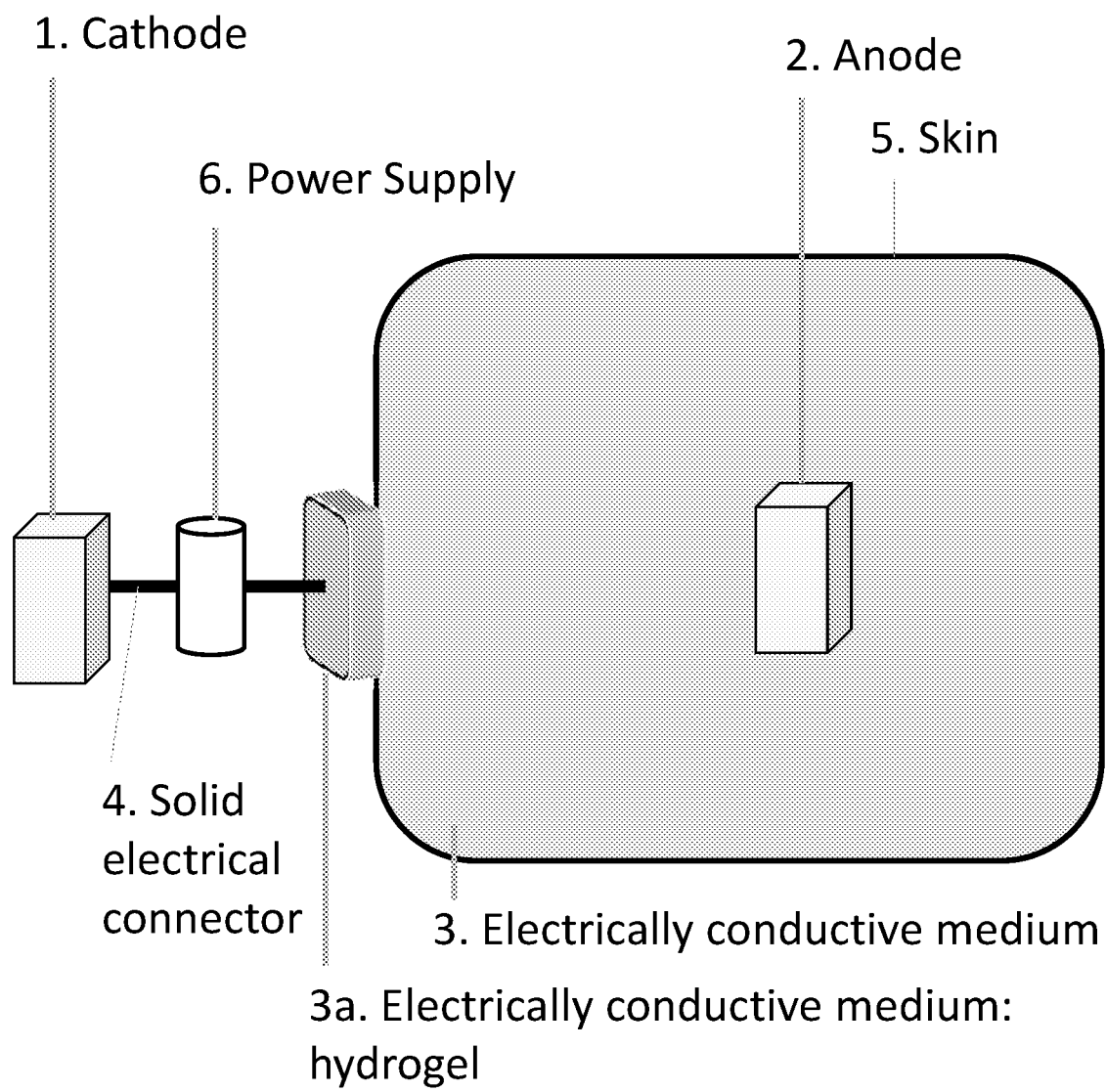
FIG. 7 is a schematic drawing showing an external powered device that includes a cathode, an electrically conductive hydrogel, and a direct current power supply, wherein the cathode and hydrogel are electrically connected via an electrically conductive connector (as shown) or by direct contact (not shown) and the hydrogel is contact with the skin.

FIG. 7 shows a configuration in which a power supply is connected to the cathode. The cathode may be in contact with the skin or to an electrically conductive medium (e.g., a hydrogel) that is in contact with the skin, as shown in FIG. 7 (a hydrogel keeps the skin conductive and makes the interface between the electrode and the skin more comfortable). The voltage supplied by the power supply in such a "powered cathode" affects the rate of reduction of the anode. In various embodiments, the power supply may be external to the body or internal (i.e., implanted). The voltage selected should be sufficient to cause a reduction in the unwanted deposit without substantially affecting healthy bone or other tissues. The system optionally includes remote monitoring and control, integral current interrupters, and other features.

FIG. 8 embodies a configuration of a device for reduction of a subdermal deposit. A cathode material (e.g., copper metal) is sandwiched between an attachment material and a conductive medium (e.g., a hydrogel). In use, the cathode material is placed in contact with the skin and the attachment material holds the device in place. Any suitable attachment material may be used, including without limitation an adhesive, adhesive patch, film, bandage, textile, fabric, clamp, brace, splint, sleeve, cast, hook-and-loop fastener (a Velcro® strip), elastic band, or combination thereof. The dimensions of this device depend on the location and nature of the unwanted deposit.

The device of FIG. 8 optionally includes electrically conductive microneedles (MN) on its skin-facing surface (see, e.g., Rzhevskiy et al., J. Controlled Release 270:184-202). MNs consist of a plurality of micro-projections, generally ranging from 25-2000 μm in height, of different shapes, which are attached to a base support, such as a patch or device. Since MNs have micron-sized dimensions, their use is relatively painless and results in no significant skin damage. MN arrays can be fabricated from a wide range of materials such as silicon, glass, metals (e.g., stainless steel, titanium, palladium, palladium-cobalt alloys, nickel, etc.), and polymers and can be further incorporated into a patch or a device. MN arrays may be fabricated at relatively low cost by various methods, such as lithography and etching, photolithography, micro molding, drawing lithography, micro-machining, laser cutting and so on (Donnelly et al., Drug Deliv. 17:187-207, 2010). The MNs may be solid or hollow.

Figure 9:
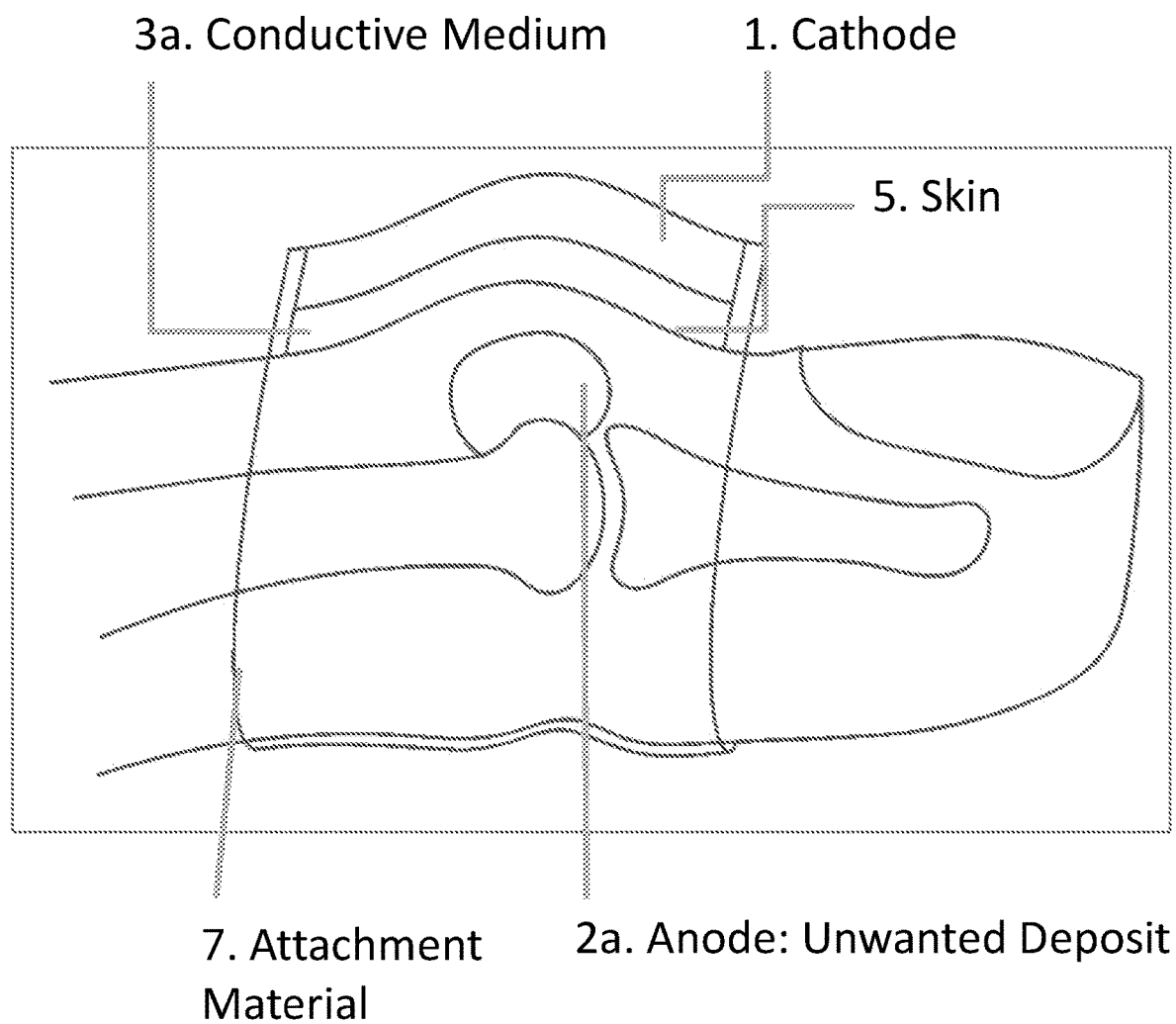
FIG. 9 shows a sectional view of the use of the device of FIG. 8 for Heberden's node reduction.

FIG. 9 shows the device of FIG. 8 placed on the skin of a finger and secured in place by the attachment material, as near as possible to the unwanted deposit (anode), in this case Heberden's node, with the attachment material, which is wrapped around the finger to secure the device in place. The unwanted deposit is reduced by the completion of the electrochemical cell. FIG. 9 demonstrates the preferred application of this method with an electrically conductive medium, a hydrogel, between the skin and a copper cathode to ensure a consistently conductive electrical connection.

With respect to the various embodiments of the invention, the effectiveness of the device for reducing or eliminating UDs may be affected by the distance between the electrode (here, the cathode) and the unwanted deposit. In some embodiments, the electrode can be in contact with the UD; in others, the electrode is positioned without about 0.01 mm to about 10 mm from the UD; or about 0.1 mm to about 5 mm. In addition, the difference in standard electrode potential between the electrode and the UD is a factor. The electrode may, for example, comprise a material with a standard electrode potential between about −4.1 and about 0 electron volts relative to the standard hydrogen electrode under standard conditions; or between about −3.9 and about −1.0 electron volts; or between about −3.8 and about −2.98 electron volts. According to some embodiments, the standard electrode potential of the electrode is greater than that of the unwanted deposit, including without limitation, from 0.001 to 7.200 electron volts greater. The electrode may be external to the animal's body, for example, in contact with the skin, or implanted via surgery, injection, iontophoresis, or other means beneath the skin of the subject, for example.

In the devices and methods of the invention, the electrode may comprise any electrically conductive material including without limitation: a single metal, multiple metals, metal oxides, an alloy of metals, a metal ceramic composite, a metal polymer composite, a chemical compound, graphite, graphene, electrically conductive composite materials (e.g., electroceramics), doped semiconductors or polymers, and mixtures thereof. Any biocompatible metal may be used, including without limitation: Actinium, Aluminium, Americium, Barium, Berkelium, Beryllium, Bismuth, Bohrium, Cadmium, Calcium, Cesium, Chromium, Cobalt, Copper, Curium, Darmastadtium, Dubnium, Dysprosium, Einsteinium, Erbium, Europium, Fermium, Francium, Gadolinium, Gallium, Gold, Hafnium, Hassium, Holmium, Indium, Iridium, Iron, Lanthanum, Lawrencium, Lead, Lithium, Lutetium, Magnesium, Manganese, Meitnerium, Mendelevium, Mercury, Molybdenum, Neodymium, Neptunium, Nickel, Niobium, Nobelium, Osmium, Palladium, Platinum, Plutonium, Polonium, Potassium, Praseodymium, Promethium, Protactinium, Radium, Rhenium, Rhodium, Roentegenium, Rubidium, Ruthenium, Rutherfordium, Samarium, Scandium, Seaborgium, Silver, Sodium, Strontium, Tantalum, Terbium, Thallium, Thorium, Thulium, Tin, Titanium, Tungsten, Ununbium, Uranium, Vanadium, Ytterbium, Yttrium, Zinc, Zirconium.

Heberden's and Bouchards' nodules; Halux Rigidus; Bone Spurs. For the applications of the invented device in fingers and toes such as Heberden's and Bouchard's nodules and Halux Rigidus, as well as similar malformations, the device is positioned in contact with or within about 0.001 cm to about 3 cm of said deposit, more specifically within about 0.01 cm to about 2 cm of said deposit, and most specifically about 0.1 cm to about 1.0 cm of said deposit.

Creating an electrical connection from the cathode (e.g., a piece of copper metal) to the skin of a person with Heberden's or Bouchard's nodules, Halux Rigidus, or Bone Spurs in the area of the nodule reduces the mass of the nodule over time. To assure continued contact between the cathode and the skin, the device may be secured in place over the nodule with athletic tape or a bandage, for example. The new growth, the nodule, has a lower electrode potential than the existing bones in the finger. Therefore, when connected electrically to a cathode, the new growth reduces, protecting the old bone. Skin is electrically conductive in most people unless it is very dry or very cold. Variations in the subject's perspiration would cause people with dryer skin to experience less UD dissolution and vice versa.

Heterotopic Ossification.

Many US soldiers return home with a disease called Heterotopic Ossification, a painful disorder wherein soft tissues that have been exposed to significant blunt force trauma (for example survivors of TED explosions at close range) develop calcium-based crystals. These crystalline formations cause pain and inflammation. The current methods for treatment include pain and inflammation management with drugs and in extreme cases, surgery for removal. The same type of unwanted growth is known to form in the tissue surrounding the remaining limb after amputation and in patients who have had knee or hip replacements. In another embodiment, the present invention is used for dissolution of such internal calcifications, e.g., heterotopic ossification of the hip joint after a hip replacement or calcium pyrophosphate crystals in the hip, knee, fingers and toes. For such applications the device is positioned in contact with the calcium pyrophosphate crystals, or, alternatively, in their vicinity, e.g., within about 0.1 cm to about 10 cm from the surface of the deposit, more specifically within about 0.5 cm to about 5 cm of said deposit, and most specifically about 0.9 cm to about 3 cm of said deposit. The closer together the anode and cathode are placed, the less likely the current produced will be diffused or redirected and more effective, faster, and complete the treatment.

For the reduction of Heterotopic Ossification in the forearm, the method described herein would be applied to the skin of the patient as close to the unwanted deposit as possible. Immediately upon completion of the electrochemical cell by providing electrical contact between the anode and the unwanted deposit within the electrically conductive body of the patient, reduction of the deposit begins and continues until the connection is disrupted.

Malformed Bone Unions.

Another application for this is the ability to dissolve malformed bone unions without surgery. A patient presents with a digit or limb that had previously broken or fractured and healed in an improper arrangement so as to interfere with normal daily activity. Application of the present invention removes recently deposited bone growth via electrochemical reduction. The electrochemical cell is created by connecting a cathode to the skin in the area of the malformation. This scenario is appropriate where the malformation is close to the skin as in fingers and toes. In some locations, such as a malformation of a tibia located many centimeters from the surface, implantation of a cathode may prove more efficient. Once the cathode is placed and electrically connected to the electrochemical cell is formed and the new bone is reduced and dissolves into the surrounding tissue and bodily fluids. The bone fracture may now be reset in the correct position for proper healing.

Pseudogout.

Calcium pyrophosphate deposition, CPPD, commonly referred to as pseudogout, involves the deposition of CPPD crystals in joints. These needle-like and angular crystals cause pain, and inflammation, acting as an abrasive inside the joint. By applying the method to the skin adjacent to the joint, the CPPD crystals are electrochemically reduced, thereby reducing the abrasion, associated inflammation and pain caused by the crystals.

Dental Tori.

Dental tori are a calcific growth inside the mouth that can be uncomfortable and may require surgery. A dental practitioner could prepare a retainer with a cathode material and if necessary an electrically conductive medium that would put the cathode in contact with the lining of the mouth in the region of the growth.

Other Conditions.

The use of this method may be extended to include the implantation via surgery or injection of the anode nearby or in direct physical contact with the unwanted deposit. For some applications, the desired target for reduction may be obscured by another object. For the formation of the electrochemical cell, implantation of the device in a position that is closer to the target, with no interference, may be preferred. In cases of implantation, the anode will be inside the electrically conductive mammalian body. Likely examples of these may include: spinal stenosis, heart valve stenosis, deep heterotopic ossifications, arterial plaque growths, ureter stenosis, kidney calcification, breast tissue calcification, tumors with calcific structures and others.

Other diseases and conditions that can be treated using the devices and methods of the present invention include, but are not limited to bone spurs and Chondrocalcinosis, soft tissue calcification (in damaged joints, blood vessels, dysfunctional areas in the brain, diseased organs, scleroderma), kidney stones, urinary stones, prostate stones, salivary stones, dental pulp stones, dental calculus, salivary stones, gall stones, pineal gland calcifications, atherosclerotic arteries and veins, coronary calcification, damaged cardiac valves, calcification on artificial heart valves, carpal tunnel and tumoral calcifications, cataracts, malacoplakia, calcified menisci, dermatomyositis, metastatic calcification of non-osseous viable tissue, "apatite diseases" (characterized by the appearance of needle-like crystals comparable to those of bone apatite in the fibrous connective tissue), spinal stenosis, heterotopic ossification (fibrodisplasia ossificans, traumatic mytosis ossificans, neurogenic heterotopic ossificans) ankylosing spondylitis, enthesophytes, myringosclerosis and intratympanic tympanosclerosis.

FIGS. 10 and 10A provide the names and uses of many materials commonly found in medical devices. Each of these materials has a unique electrode potential that is different from animal bone.

FIG. 11 provides a quick reference chart based on standard electrode potentials for choosing materials for anodes and cathodes in devices and methods of the present invention For the applications of the invented device, the operating temperature for this method is about −2° C. to 120° C., more specifically 0° C. to 95° C. and most specifically between a low of 6.2° C. and a high of 40.55° C.

Reducing the Mass of or Eliminating Implanted Materials

Material that is derived from sources outside of the animal body can also be targeted for dissolution using the present invention. Once an optimal period of use is determined for the patient's medical concern, the stent or other implant (serving as an anode) can be intentionally reduced and/or eliminated by selection of a cathode having an appropriate standard electric potential, which can be facilitated by the use of a power supply that provides direct current at a selected voltage. This allows the medical team to choose when to dissolve the stent. This would be a significant advantage in stents, splints, supports, staples, screws, bolts, rods, retainers, brackets, braces, clasps, closures, clamps, stays, markers and other hardware used internally that is not needed once healing is complete and the hardware is no longer needed. Other extrinsic material that has been introduced into the body, such as shrapnel, for example, can also be targeted for dissolution using the present invention.

Modulating Bone Loss Resulting from Implanted Materials

Devices and methods are also provided for decreasing or eliminating bone loss resulting from implanted materials. Orthopedic surgeons use implants for a variety of surgical procedures, including without limitation reconstructing a damaged joint, repairing a fractured bone, or altering the alignment of the skeleton. Implants are substances that are placed inside or on the surface of the body. In the field of orthopedics and in foot and ankle surgery in particular, implants refer to objects which are used to hold bones together, strengthen tendons and ligaments or attach them to bone, and replace bone. Non-biologic implants include, but are not limited to, metal plates, screws, pins, intramedullary rods inserted into the cavity of a bone, medical devices, etc. Common materials for implants include without limitation titanium, stainless steel, ceramics, and polyethylene.

ASTM F3044-14 provides a standard method for evaluating the potential for galvanic corrosion for medical implants (ASTM F3044-14, "Test Method for Standard Test Method for Evaluating the Potential for Galvanic Corrosion for Medical Implants," ASTM International, West Conshohocken, Pa., 2014, www.astm.org).

Currently used artificial hip joints are mainly composed of a femoral head of monolithic alumina or alumina-zirconia composites articulating against a cross-linked polyethylene liner of acetabular cup or Co—Cr alloy in a self-mated configuration. Alternative materials are dense alumina ceramic and titanium-6% aluminum-4% vanadium (Ti-6Al-4V) alloys for the femoral head and the stem, respectively. In some cases, thin ultra-hard diamond-based, TiN coatings on Ti-6A-4V or thin zirconia layer on the Zr—Nb alloy have been fabricated to develop high wear resistant bearing surfaces. Similarly, knee implants are made of metal alloys, ceramic material, or strong plastic parts.

Bone loss, or osteolysis, is a known complication of hip replacement. When the metal implant is placed in contact with the femur bone inside the body, bone loss occurs. As a result, the implant components loosen and a second hip replacement surgery may be necessary.

In one embodiment an impressed current protection system is used to preserve the bone in a metal/bone contact area or elsewhere near the implant in and around a joint or other site in the body. During the installation of the prosthetic or other implanted material, electrical connections to the bone, the prosthetic or a new electrode are implanted. The power supply is either implanted completely or connected to the system that includes a power supply that provides direct current at a selected voltage via electrically conductive leads to the skin of the patient where they can be connected to the power supply.

Another embodiment of the invention is the application of coatings as an electrode in the form of metals, paint, plastics or ceramics to achieve the desired result. In hip replacement prosthetics the dissolution of bone occurs at the interface between the bone material and the metallic implant, which may or may not also include cement. The area where the dissolution occurs is inside the joint, an area surrounded by conductive medium. By applying a coating to the surface of the implant that has a lower electrochemical potential than the bone, the coating will be dissolved in the galvanic cell.

Another embodiment of the invention is to coat the exterior of the implant, particularly any surface of the implant that is in electrical connection with the bone (whether through direct contact or indirectly through contact with a conductive medium such as an electrically conductive body fluid) with an electrically nonconductive coating material (i.e., an electrical insulator), including without limitation a non-conductive polymer, ceramic, or other biocompatible material. Such a coating reduces or eliminates bone loss due to electrochemistry as compared with a similar medical implant lacking the coating.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The invention is further illustrated by the following examples. The examples are provided for illustrative purposes only. They are not to be construed as limiting the scope or content of the invention in any way.

EXAMPLES

Example 1: An Electrochemical Cell with Bone (Anode) and Copper Metal (Cathode)

Two glass sample jars were filled with a bone sample and a piece of copper. In the control jar distilled water was added. In the experimental jar, salt (NaCl) was added to the distilled water. Once the experiment was complete, relative rates of dissolution were determined via visual inspection of the two sample jars. In the test jar with conductive salted water, the bone sample was reduced in the presence of copper and dissolved into the solution faster than the bone in the much less conductive control jar.

Example 2: Measurement of Current Resulting from an Electrochemical Cell with Bone (Anode) and Platinum Wire (Cathode)

Figure 13:
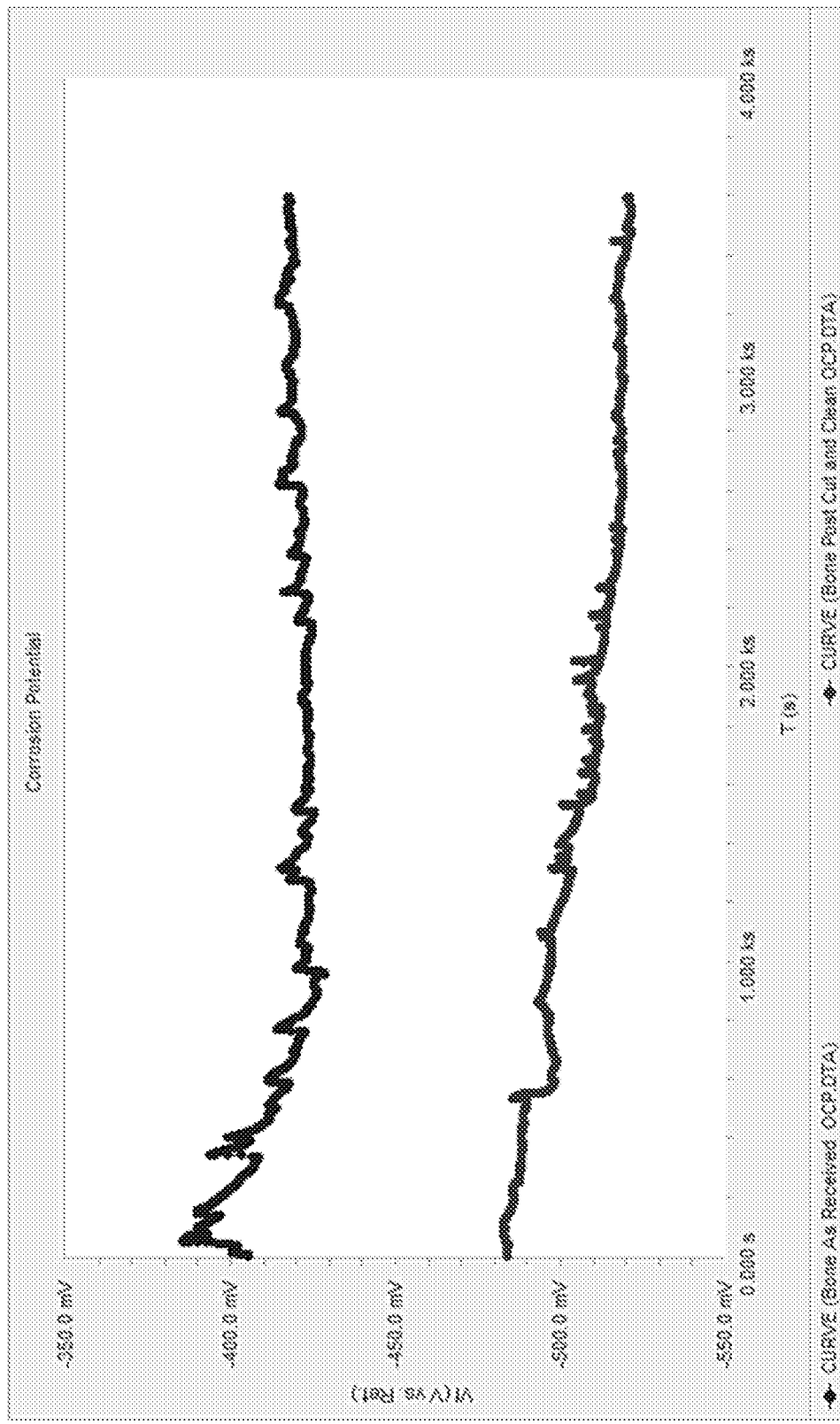
FIG. 13 shows open circuit measurements in an electrochemical cell in which cut and cleaned bone was measured versus a saturated calomel electrode (SCE).
Figure 14:
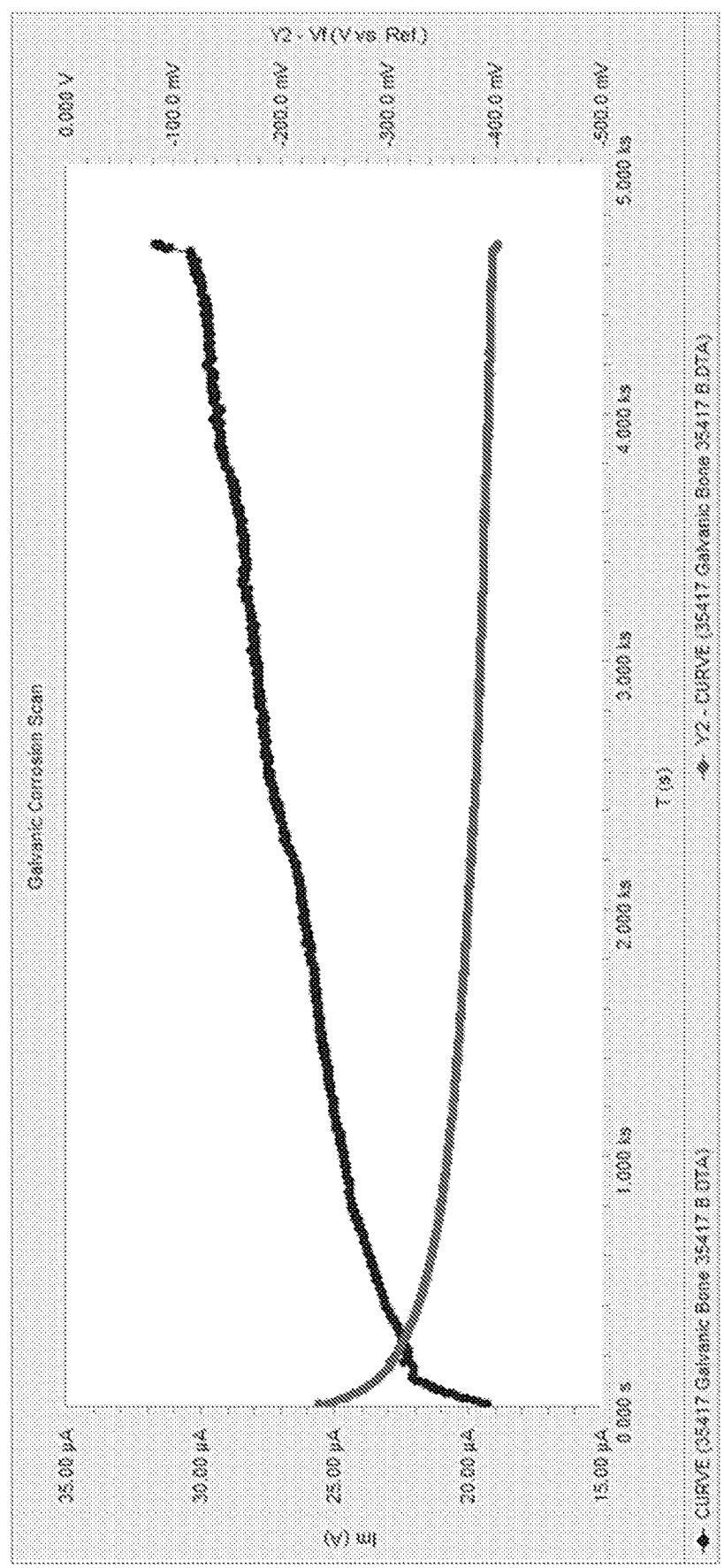
FIG. 14 shows a galvanic corrosion scan resulting from a electrochemical cell in which the anode was cut and cleaned bone and the cathode was a platinum rod.

Test cells were set up as described in ASTM F3044-14, "Test Method for Standard Test Method for Evaluating the Potential for Galvanic Corrosion for Medical Implants," ASTM International, West Conshohocken, Pa., 2014 (www.astm.org). A beef bone ("As Received") was tested, as well as a section of the beef bone (including marrow) approximately 2 inches in length that was prepared by shaving off the outer layer of the bone ("Post Cut and Clean"). First, an open circuit measurement was taken in which the bone samples were measured versus a saturated calomel electrode (SCE). The open circuit potential was measured as approximately −520 mV for the "Post Cut and Clean" bone sample (FIG. 13). Next, the bone was tested in a cell in which the bone was used as the anode and a platinum rod as the cathode. The cell was run for one hour under aerated conditions in phosphate buffered saline at 37° C. A galvanic interaction was observed between the post cut and clean bone sample and platinum counter-electrode. As shown in FIG. 14, a considerable current was observed.

What is claimed is:

1. A device for eliminating or decreasing the mass of an unwanted deposit in the body of an animal comprising:
   (a) an electrode comprising a material having an electrode potential that is greater than that of the unwanted deposit; and
   (b) a power supply that is electrically connected with the electrode, wherein the power supply is configured to provide direct current at a selected voltage;
   wherein the electrode is configured to contact the animal's skin;
   wherein the electrode is configured to contact or to be in electrical connection with the unwanted deposit; and
   wherein the unwanted deposit is a calcium based deposit.

2. The device of claim 1 wherein the electrode has a surface comprising electrically conductive microneedles configured to penetrate the animal's skin.

3. The device of claim 1 wherein the device comprises an electrically conductive layer that has a first surface in contact or in electrical connection with the electrode and a second surface configured to contact the skin of the animal.

4. The device of claim 3 wherein the second surface of the layer comprises electrically conductive microneedles configured to penetrate the skin.

5. The device of claim 1 comprising an attachment material for maintaining contact of the electrode with the skin of the animal.

6. The device of claim 1 wherein the electrode is in contact with the unwanted deposit.

7. The device of claim 1 wherein the electrode is configured to be connected to the unwanted deposit by an electrically conductive connector.

8. The device of claim 7 wherein the electrically conductive connector is an insulated wire.

9. A method for eliminating or decreasing the mass of a unwanted deposit in the body of an animal, the method comprising: contacting the electrode with the animal's skin, wherein the electrode is placed in electrical connection with the unwanted deposit, wherein the electrode comprises a material having an electrode potential that is greater than that of the unwanted deposit, wherein the electrode is electrically connected with a source of direct current at a selected voltage, and wherein the unwanted deposit is a calcium based deposit.

10. The method of claim 9 wherein the electrode is in contact with an electrically conductive layer that has a surface in contact with the animal's skin.

11. The method of claim 9 comprising contacting the electrode with the unwanted deposit.

12. The method of claim 9 comprising connecting the electrode to the unwanted deposit with an electrically conductive connector.

* * * * *